(12) United States Patent
Negre et al.

(10) Patent No.: US 8,177,737 B2
(45) Date of Patent: May 15, 2012

(54) DRAINAGE SYSTEM FOR TREATING HYDROCEPHALUS

(75) Inventors: Philippe Negre, Paris (FR); Olivier Bonnal, Melsungel (DE)

(73) Assignee: Sophysa, Orsay (FR)

( * ) Notice: Subject to any disclaimer, the term of this patent is extended or adjusted under 35 U.S.C. 154(b) by 485 days.

(21) Appl. No.: 12/161,493

(22) PCT Filed: Jan. 26, 2007

(86) PCT No.: PCT/FR2007/050699
§ 371 (c)(1),
(2), (4) Date: Oct. 6, 2009

(87) PCT Pub. No.: WO2007/085771
PCT Pub. Date: Aug. 2, 2007

(65) Prior Publication Data
US 2010/0056980 A1 Mar. 4, 2010

(30) Foreign Application Priority Data
Jan. 26, 2006 (FR) ...................................... 06 50284

(51) Int. Cl.
*A61M 5/00* (2006.01)
*F16K 31/12* (2006.01)
(52) U.S. Cl. ............ 604/9; 604/8; 137/505.12; 137/506
(58) Field of Classification Search .................. 604/8, 9; 137/504, 505.12, 506, 508
See application file for complete search history.

(56) References Cited

U.S. PATENT DOCUMENTS

| 4,106,510 A | * | 8/1978 | Hakim et al. ...................... 604/9 |
| 4,605,395 A | | 8/1986 | Rose et al. |
| 4,621,654 A | | 11/1986 | Holter |
| 4,681,559 A | | 7/1987 | Hooven |
| 4,776,839 A | * | 10/1988 | Doumenis ......................... 604/9 |
| 5,336,166 A | * | 8/1994 | Sierra ................................. 604/9 |
| 6,126,628 A | * | 10/2000 | Nissels ............................. 604/9 |
| 6,689,085 B1 | | 2/2004 | Rubenstein et al. |

FOREIGN PATENT DOCUMENTS

| DE | 195 41 377 A1 | 6/1996 |
| EP | 0 115 973 A1 | 8/1984 |
| EP | 0 688 575 A1 | 12/1995 |
| FR | 2 685 206 A1 | 6/1993 |
| WO | WO 01/54752 A1 | 8/2001 |

\* cited by examiner

*Primary Examiner* — Leslie Deak
(74) *Attorney, Agent, or Firm* — Oliff & Berridge, PLC (57) ABSTRACT

The present invention relates to a drainage device comprising:
an internal chamber;
at least one inlet port and at least one outlet port communicating with the internal chamber;
a shutter disposed at least in part in the internal chamber;
at least one first valve seat associated with the inlet port, the shutter being capable of bearing against the first seat in order to isolate the inlet port from the outlet port, in particular when the pressure difference between the inlet and outlet ports is less than a predetermined first opening pressure; and
at least one flow constriction associated with the outlet port, the shutter being capable of shutting said constriction, while allowing a minimum, safety flow to pass at a rate that is greater than or equal to 2.5 mL/h even in a maximally-shut position, referred to as a "closed" position, which position is reached in particular for pressure differences between the inlet and outlet ports that are greater than or equal to a predetermined closure pressure.

31 Claims, 7 Drawing Sheets

DRAINAGE SYSTEM FOR TREATING HYDROCEPHALUS

The present invention relates to a drainage system for treating hydrocephalus.

Certain patients fitted with a hydrocephalus valve can suffer from hyderdrainage symptoms when they pass from the prone position to the sitting or standing position. This phenomenon is known as the "siphon effect" and results from the hydrostatic pressure, i.e. the weight of the water column, that becomes established between the proximal end of the shunt at brain level and its distal end at abdominal level, on the patient moving into the vertical position. The sudden change in intracranial pressure which thus passes from a positive value to a value that is strongly negative, leads to an excessive quantity of cerebrospinal liquid draining through the valve from the cerebral ventricles towards the peritoneum.

Hyperdrainage can lead to various complications, such as a reduction in ventricle size, the appearance of slit ventricles, and the formation of subdural hematomas or of hygromas.

Numerous devices have been proposed for combating the siphon effect:

gravitational devices making use of the weight of one or more tantalum or steel balls for increasing the resistance of the valve when the patient sits or stands up (Horizontal Vertical valve and GCA device sold by the supplier Integra, Chhabra Z-Flow valve sold by the supplier Surgiwear, Dual-Switch valve, paedi-GAV, proGAv, Shunt Assistant sold by the supplier Miethke). The drawback of such devices is that they do not operate properly if they shift from their vertical axis after they have been implanted or if the patient undertakes physical exercise that might cause the ball to move up and down (jogging);

diaphragm devices of the Anti-Siphon Device (ASD) type sold by the supplier Heyer-Schulte, Siphon Control Device (SCD) or Delta Chamber sold by the supplier Metronic PS Medical, relying on the movement of a silicone diaphragm when the pressure difference across the terminals of the valve becomes less than atmospheric pressure. By their very design, those devices are particularly sensitive to implantation position. If the anti-siphon device is implanted lower than the inlet end of the ventricular catheter, there is a risk of hyperdrainage, and conversely there is a risk of hypodrainage if the device is implanted higher than the end of the ventricular catheter. Those devices also need to be capable of detecting atmospheric pressure through the skin that covers them. A thick skin, or scar tissue forming over the device, can inactivate it. Such devices are also highly sensitive to any increase in subcutaneous pressure, e.g. caused by the head resting on a pillow. Furthermore, those devices are connected in series relative to a differential pressure valve so their resistance is added to that of the valve when the patient is in a vertical position, which leads automatically to an increase in the intracranial pressure in the standing position compared with the prone position. Such devices therefore operate in a non-physiological manner, since with a normal individual it is found on the contrary that intracranial pressure becomes lower when going from the prone position to the standing position; and flow rate regulator devices of the Orbis Sigma type. A device of that type presents a large amount of hydrodynamic resistance in its flow control position because it has a small flow section, thus making it particularly sensitive to the risk of becoming clogged by debris of cerebral origin or by protein deposits. That device, designed to limit the flow rate to the mean value at which cerebrospinal liquid is produced, i.e. 20 milliliters per hour (mL/h), is not capable of absorbing the large physiological increases in flow rate (up to 116 mL/h) that occur during sleep as a result of cerebral vasogenic pressure waves or during stages of rapid eye movement, or indeed that are caused by coughing fits, without intracranial pressure increasing excessively. That system can therefore lead to hypodrainage, not only in the prone position, but also in the standing position when the hydrostatic pressure remains below the resistance of the valve, as can happen with young children.

The SiphonGuard™ device sold by the supplier Codman and described in particular in U.S. Pat. No. 6,126,628 is for connecting in series with a differential pressure valve that is preset or adjustable. It has a main passage without resistance that is controlled by a normally-open valve, and a secondary passage with high resistance that is constituted by a long spiral-wound path of small diameter. When the drainage flow rate is low, the liquid flows both via the main passage and via the secondary passage. When the flow rate exceeds a certain threshold, in particular when the patient gets up, the valve closes and constrains the liquid to flow via the high resistance secondary passage that is calibrated to limit flow rate. A drawback is that in the event of an abnormal increase in intracranial pressure, the device then becomes incapable of opening to reestablish a normal pressure in the ventricles. Furthermore, the small section of the high resistance secondary passage makes the device particularly vulnerable to becoming obstructed by cerebral debris or by protein deposits, with there being a risk of the device becoming permanently blocked in a high resistance position by a closed compartment being created between the differential pressure valve and the valve that closes the main path. Finally, since that device is connected in series, its resistance is additional to that of the differential pressure valve in which it is connected. That means that the threshold for closure of the main path that triggers flow rate limiting cannot be set independently of the pressure at which the differential pressure valve opens. As a result, a tall patient with high hydrostatic pressure in the standing position will need to have the valve adjusted for high pressure, with the risk of presenting hypodrainage in the prone position, while a short patient with low hydrostatic pressure will need to have the valve adjusted to low pressure, with a risk of hyperdrainage occurring in the prone position.

U.S. Pat. No. 5,336,166 discloses a system having first and second pressure regulator valves together with a flow rate regulator valve. The first pressure regulator valve is connected in series with the assembly formed by the other two valves connected in parallel. Alternatively, the second pressure regulator valve can be connected in parallel with an assembly formed by the other two valves in series. That system thus enables a constant regulated pressure or a constant regulated flow rate to be obtained, depending on the pressures applied to the system. In particular, between the moment when the first pressure regulator valve opens and the moment when the second pressure regulator valve opens, the flow rate of cerebrospinal fluid through the drainage system remains substantially constant, which corresponds to the therapeutic operation of the system. When the drainage system is configured to regulate flow rate at 5 mL/h and is implanted in a patient presenting a fluid flow rate of about 20 mL/h, the occurrence of excessive intracranial pressure outside the operating zone for flow rate regulation can lead to certain symptoms and can require a new drainage system to be implanted.

Patent EP 0 688 575 discloses a subcutaneous valve enabling a liquid distribution or passage to be externally regulated, the valve comprising a rotor and two micromagnets mounted thereon.

The invention provides a drainage device comprising:
- an internal chamber;
- at least one inlet port and at least one outlet port communicating with the internal chamber;
- a shutter disposed at least in part in the internal chamber;
- at least one first valve seat associated with the inlet port, the shutter being capable of bearing against the first seat in order to isolate the inlet port from the outlet port, in particular when the pressure difference between the inlet and outlet ports is less than a predetermined first opening pressure; and
- at least one flow constriction associated with the outlet port, the shutter being capable of shutting said constriction, while allowing a minimum, safety flow to pass at a rate that is greater than or equal to 2.5 mL/h even in a maximally-shut position, referred to as a "closed" position, which position is reached in particular for pressure differences between the inlet and outlet ports that are greater than or equal to a predetermined closure pressure.

As explained in greater detail in the description below, this drainage device can present at least one of the following advantages:
- enabling adjustment of a pressure level in the standing position that is independent of a pressure level in the prone position;
- enabling the system to operate independently of subcutaneous pressure, of atmospheric pressure, of the position of the valve, and of gravity;
- enabling the pressure regulation function in the prone position to be dissociated from the same function in the standing position, these functions being provided in particular by two different mechanisms that are independent of each other, thereby providing reliability and safety in the face of any risk of obstruction;
- making a plurality of pressure regulation levels possible as a function of the position of the patient, in particular standing or prone;
- enabling one or more pressure levels to be adjusted, in particular by a doctor, after the device has been implanted in a patient; and
- limiting the risk of the drainage device being obstructed by debris or by organic deposits, thereby limiting the risk of the need to implant a new drainage device in the patient.

Finally, the shutter and the flow constriction are shaped in such a manner as to allow the flow constriction to be shut only partially. Advantageously, having no totally-shut position enables the hysteresis between opening and partial closure of this flow constriction to be diminished.

Preferably, the drainage device of the invention includes one or more of the following optional characteristics:
- the safety minimum flow rate is less than 20 mL/h;
- the shutter and the edge of the flow constriction are shaped in such a manner as to define, in the maximally-shut position, a flow section between the shutter and the edge of the flow constriction such that the safety minimum flow rate in this position, as measured using deionized water at 37° C., is greater than 2.5 mL/h, and preferably less than 20 mL/h;
- preferably, the progressive shutting of the flow constriction leads to a decrease in flow rate and to an increase in pressure;
- preferably, this flow section extends substantially perpendicularly to the travel direction of the shutter in the vicinity of the maximally-closed position. Thus, in this position, the fluid flows substantially parallel to the travel direction of the shutter going past the flow constriction. It thus constitutes a "buffer" of fluid between the shutter and the flow constriction which is particularly effective in decreasing hysteresis;
- the first valve and the flow constriction, possibly after optional adjustment, are preferably unchanging relative to the body defining the internal chamber, with the shutter being movable relative to said body;
- also preferably, the shutter is in the form of a body of revolution about its main travel axis A, and is preferably a ball. The shutter is preferably movable perpendicularly to said axis. Advantageously, such a shape for the shutter enables it to be self-centering under the effect of the fluid flow, thereby limiting friction with the edge of the flow constriction;
- advantageously, the device may include a return spring arranged to exert a force on a shutter-forming ball tending to urge it against the first seat, the ball being arranged to be capable of being moved towards said flow constriction against the force exerted by the spring. The spring preferably includes at least a frustoconical base portion that enlarges towards the bottom end of the spring and a cylindrical top portion that is connected to said frustoconical face portion;
- upstream from the flow constriction, the internal chamber presents the shape of a truncated cone flaring upstream relative to the flow direction, and/or extends downstream from the flow constriction in the form of a truncated cone flaring downstream in the flow direction, with the half-angle β at the apex being greater than the half-angle α at the apex of the upstream truncated cone. Advantageously, and surprisingly, the hourglass-shape formed by the upstream and downstream truncated cones diminishes hysteresis between opening and closing the flow constriction;
- the drainage device is shaped in such a manner that, on the pressure difference increasing, said shutter does not begin to reduce the flow rate through the device unless said flow rate is less than 30 mL/h, and/or in such a manner that the first opening pressure is less than the initial pressure difference;
- the drainage device includes a branch port communicating with the internal chamber, the inlet and branch ports communicating with each other and being isolated in part from the outlet port by the shutter shutting the flow constriction;
- the shutter and the flow constriction are shaped in such a manner that the shutter can go through the flow constriction, preferably without friction, when the pressure difference exceeds a so-called "high-pressure" opening pressure that is greater than said closure pressure, and in particular at least 10% greater. The spacing between the shutter and the flow constriction in the position in which the shutter is closing the flow constriction to the maximum extent is preferably constant, i.e. in said closed position, the flow section presents a width that is constant all around the shutter. Advantageously, this reduces the risk of friction between the shutter and the flow constriction, and thus the risk of hysteresis between opening and closing said flow constriction;

the drainage device is shaped in such a manner as to prevent a drainage flow rate that is greater than 20 mL/h if the pressure difference does not exceed said high-pressure opening pressure;

also preferably, the partial-shutting drainage device of the invention is shaped in such a manner that when the pressure difference increases, said shutter begins to reduce the flow rate through the second valve seat only if the flow rate is less than 30 mL/h;

advantageously, it is thus possible to drain the cerebrospinal liquid significantly even when the pressure difference is small, providing it is greater than the first opening pressure. When the patient is in the prone position this serves to limit the risks of hypodrainage;

the first opening pressure and/or the closing pressure and/or the high-pressure opening pressure is/are preferably adjustable, with it being possible to make such adjustment(s) in particular without making contact. In an advantageous embodiment, adjustment is performed via magnetic coupling. The device then includes means enabling it to couple magnetically with the outside of the patient's body in order to perform the adjustment(s);

adjustment by means of a motor that receives control instructions and/or power via radiofrequency waves is also possible. Advantageously, the drainage system can thus be positioned at a distance from the skin; and in variants of the invention, the shutter takes the form of a diaphragm or of a resilient blade that are suitable for shutting the flow constriction, while nevertheless allowing a safety minimum flow rate to pass.

In another embodiment, the flow constriction constitutes a second valve seat against which the shutter can bear, the shutter and the second valve seat forming a second valve that is capable of closing, while continuing to allow a safety minimum flow rate to pass in operation, at a predetermined closure pressure that is greater than the first opening pressure, and preferably at least 10% greater.

The drainage device may include at least one elastically deformable diaphragm having at least a portion that defines the shutter. In particular, the diaphragm may include:

a central passage arranged to allow fluid to pass through; and bottom and top lips substantially adjacent to the central passage, the bottom and top lips extending respectively from bottom and top faces of the diaphragm, the bottom and top lips being capable of bearing against respective ones of the valve seats as a function of the deformation of the diaphragm, the lips thus defining the shutter. The bottom and top lips may extend close to or adjacent to an outline of the diaphragm. The lip providing closure of the drainage device at the closure pressure is shaped to allow a safety minimum flow rate to pass when in the closed position.

Alternatively, the drainage device may include an elastically deformable blade having a first portion that is held firmly in the internal chamber and a second portion that is movable between first and second positions in which the blade bears respectively against the first seat and against the second seat, the movable second portion of the blade thus defining the shutter.

The second seat and the blade are shaped in such a manner as to allow a safety minimum flow rate to pass in the closed position.

The invention also provides a drainage system for treating hydrocephalus, the system comprising:

at least one group of valves comprising:

a first valve for regulating pressure capable of opening at a predetermined first opening pressure to allow fluid to pass;

a second valve capable of closing while passing a safety minimum flow rate, at a predetermined closure pressure greater than the first opening pressure, the first and second valves being arranged in such a manner that the fluid can be drained through the second valve when the fluid pressure lies between the first opening pressure and the closure pressure; and a third valve for regulating pressure capable of opening at a predetermined second opening pressure that is greater than the closure pressure, preferably by at least 10%, more preferably by at least 20%, the second and third valves being arranged in such a manner that when the second valve is closed, while allowing said safety minimum flow rate to pass, fluid can be drained through the third valve.

The third valve may be an adjustable pressure regulator valve, e.g. of the Polaris® type fabricated by the supplier Sophysa (France).

Various embodiments can be envisaged. In particular, the first and second valves could be connected in series, the first valve being upstream from the second, with the third valve being connected in parallel with the group formed by the first and second valves.

The drainage system may also include a drainage device providing partial shutting or "closure" in accordance with the invention as defined above, i.e. ensuring a minimum safety flow rate in the maximally-shut closed position of the flow constriction associated with the outlet port, the shutter of said device co-operating with the first valve seat and with the flow constriction to define the first and second valves respectively of the group of valves.

When the shutter of the drainage device can go past the flow constriction, the device can also open under the effect of the "high-pressure" opening pressure that is greater than the closure pressure. The shutter of said device can then co-operate with the first valve seat to define the first valve, and with the flow constriction to define the second and third valves, the high-pressure opening pressure constituting said second opening pressure for the third valve.

The second and third valves may also be connected in parallel, with the first valve being connected in series with the assembly formed by the second and third valves, upstream from said assembly.

The drainage system may also comprise a succession of groups of valves, each group being formed by a first valve for regulating pressure and by a second valve, the first opening pressure associated with the first valve of a given group being greater than the closure pressure associated with the second valve of the preceding group. In particular, the system may have at least two groups of valves, the two groups of valve and the third valve all being connected in parallel. Each group may comprise an inlet port, a branch port, and an outlet port, the inlet port of a first group of valves being connected to the branch port of a second group of valves, and the third valve being connected to the branch port of the first group of valves.

In all of the embodiments of the invention described above, the shutter cannot close said flow constriction totally, i.e. when in the maximally-shut closed position, the closure of the flow constriction is only partial. The flow rate through the constriction, in the closed position, is then greater than 2.5 mL/h. In the present description, a flow rate greater than 2.5 mL/h is referred to as the "safety minimum flow rate".

The invention also provides a drainage system for treating hydrocephalus, the system comprising:

at least one group of valves forming in particular a hydrostatic switch and comprising:

a first valve for regulating pressure capable of opening at a predetermined first opening pressure and enabling fluid to pass through; and         a second valve capable of closing at a predetermined closure pressure greater than the first opening pressure, in particular at least 10% or 20% greater, the first and second valves being arranged in such a manner that fluid can be drained through the second valve when the fluid pressure lies between the first opening pressure and the closure pressure; and     a third valve for regulating pressure that is capable of opening at a predetermined second opening pressure that is greater than the closure pressure, in particular at least 10% greater, the second and third valves being arranged in such a manner that when the second valve is closed, fluid can be drained through the third valve.

At least one of the opening and closure pressures is pre-set, e.g. during fabrication of the corresponding valve.

The first opening pressure is advantageously selected to lie in the range 30 millimeters of water (mm $H_2O$) to 130 mm $H_2O$, and in particular in the range 40 mm $H_2O$ to 60 mm $H_2O$.

The closure pressure is selected in lie in the range 80 mm $H_2O$ to 120 mm $H_2O$, for example.

In an embodiment of the invention, the difference between the closure pressure and the first opening pressure is less than twice said first opening pressure, and in particular less than said first opening pressure.

In the invention, the first valve for regulating the pressure enables the drainage system to operate effectively while the patient is in the prone position, with a drainage flow rate that can be as great as at least 20 mL/h, or indeed at least 30 mL/h, in particular, so long as the pressure lies between the first opening pressure and the closure pressure, while the third valve for regulating pressure serves to provide effective operation to the system when the patient is in the standing position, with a drainage flow rate that can reach in particular at least 20 mL/h, or even at least 30 mL/h, providing the pressure is greater than the second opening pressure.

The drainage system of the invention serves to avoid operating with flow rate regulation, as happens with the system described in U.S. Pat. No. 5,336,166.

The valve group forming a hydrostatic switch of the invention is preferably arranged in such a manner that the flow rate of the fluid drained through the valve group is substantially zero, e.g. with a flow rate of less than 2.4 mL/h, when the pressure of the fluid is greater than the closure pressure, unlike for example the device described in U.S. Pat. No. 6,126,628 which presents a drainage flow rate corresponding to a constant resistance when the pressure is greater than the closure pressure.

In an embodiment of the invention, the first and second valves are connected in series, the first valve being upstream from the second, and the third valve is connected in parallel with the group comprising the first and second valves forming a hydrostatic switch.

This configuration makes it possible to conserve a drainage path that is always free, in the event of one of the two paths becoming obstructed.

The third valve may be a high-pressure differential valve.

When the patient is in the prone position, the cerebrospinal fluid flows via the low pressure first valve which offers less resistance. When the patient rises, there occurs a sudden hydrostatic pressure drop downstream from the first valve because of the fluid column formed between the end of a proximal catheter and the end of a distal catheter. The resulting increase in differential pressure causes the second valve to close, thereby constraining the fluid to pass via the high resistance parallel circuit constituted by the high pressure, third valve. The assembly can thus constitute an automatic hydrostatic switch that is activated solely by the change in pressure difference existing in the circuit, and totally independently of subcutaneous pressure, of atmospheric pressure, and of the position of the valve relative to the earth's gravitational field.

In a variant, the second and third valves are connected in parallel and the first valve is connected in series with the assembly formed by the second and third valves, upstream from said assembly.

The valve group forming the hydrostatic switch can thus be used in parallel with an existing preset or adjustable differential pressure valve. The assembly then constitutes a variable-resistance system capable of switching automatically from a low pressure regulator valve to a high pressure regulator valve, and vice versa, as a function of the position of the patient.

The valve group forming the hydrostatic switch can also be incorporated in a common housing with a set or programmable valve mechanism.

Advantageously, the third valve is arranged in such a manner that the second opening pressure that is associated therewith is adjustable, which adjustment can be performed in particular without contact.

By way of example, the third valve may be arranged to enable the second opening pressure to be set on a value selected from amongst N pressure levels, where N is an integer.

By way of example, the second opening pressure may be set by the doctor as a function of the size of the patient and/or of other medical parameters.

The invention makes it possible to have a drainage system that does not include a magnet, in particular that does not include a magnet for enabling an opening pressure of the drainage system to be adjusted from the outside.

The lack of a magnet makes it possible to avoid any risk of the drainage system being maladjusted when the patient is subjected to high magnetic fields, such as those generated by a nuclear magnetic resonance (NMR) imaging device.

In addition, the absence of a magnet makes it possible to make the drainage system out of materials that are not magnetic, such as a plastics material or Phynox.

In particular, the system of the invention can be made at low cost.

In an embodiment of the invention, the system comprises a succession of valve groups, each formed by a first valve for regulating pressure and a second valve, the first opening pressure associated with the first valve of a given group being greater than the closure pressure associated with the second valve of the preceding group.

Such a configuration makes it possible to have a range of predetermined opening and closure pressure levels, the drainage system of the invention thus being capable of automatically adjusting its type of operation, e.g. as a function of the size of the patient and/or the patient's position.

This configuration also makes it possible to avoid any need to adjust the drainage system before or after it has been implanted in the patient, and also presents reduced sensitivity to a drainage path becoming obstructed.

Where appropriate, the system may include at least two valve groups, these two valve groups and the third valve all being connected in parallel.

This configuration makes it possible to conserve one or more drainage paths that remain free, in the event of one of the paths becoming obstructed.

In a variant, the system comprises at least two valve groups, each group having an inlet port, a branch port, and an outlet port, the inlet port of a first one of the groups being connected to the branch port of a second one of the valve groups, the third valve being connected to the branch port of the first valve group.

In an embodiment of the invention, the valve group includes a drainage device comprising:
- an internal chamber;
- at least one inlet port and at least one outlet port communicating with the internal chamber;
- at least one shutter disposed at least in part in the internal chamber; and
- at least first and second valve seats, the shutter cooperating with the first and second valve seats to define the first and second valves respectively of the group of valves.

Where appropriate, the device may include a branch port communicating with the internal chamber. When the shutter bears against the second seat, the inlet and branch ports are in communication with each other and they are isolated from the outlet port.

The drainage device and the third valve may be incorporated within a common housing, or in a variant, the drainage device may be separated from the third valve and connected thereto by a duct, in particular a flexible duct such as an elastomer duct.

By way of example, the duct may have two lumens or two channels.

In an embodiment of the invention, the shutter comprises a ball and the device includes a resilient return member arranged to exert a force on the shutter urging it to press against the first seat. The shutter can be arranged to be capable of being moved towards the second seat against the force exerted by the resilient return member.

By way of example, the seats may be frustoconical in shape.

Advantageously, the resilient return member comprises a spring, in particular a helical spring.

The spring is preferably calibrated for low pressure.

The spring may include at least one conical or frustoconical portion, and in particular a cylindrical top portion that connects to a frustoconical base portion that becomes larger going towards the bottom end of the spring.

The ball can thus be in contact with a spring portion that presents a diameter that is relatively small, while the frustoconical base portion of the spring can serve, when the spring is compressed, e.g. while setting opening and/or closure pressure levels, to provide self-centering of the spring on its support by increasing the diameter of the frustoconical portion.

In addition, the relatively large diameter of the frustoconical base portion can serve to increase the sensitivity of the spring and thus encourage large-amplitude movements of the shutter. This makes it possible to limit the risk of the corresponding port becoming obstructed.

In an embodiment of the invention, the device includes at least one elastically deformable diaphragm having at least a portion that defines the shutter.

By way of example, the elastically deformable diaphragm may include:
- a central passage arranged to allow fluid to pass through; and
- bottom and top lips, in particular annular lips, placed substantially around the central passage, the bottom and top lips extending from bottom and top faces respectively of the diaphragm. The bottom and top lips can bear against respective ones of the valve seats depending on the deformation of the diaphragm, with the lips thus defining the shutter.

In a variant, the elastically deformable diaphragm may include bottom and top lips, in particular annular lips, that extend in the proximity of or adjacent to an outlet of the diaphragm. The bottom and top lips can bear against respective ones of the valve seats, depending on the deformation of the diaphragm, with the lips thus defining the shutter.

By way of example, the diaphragm may be made of elastomer and where appropriate may be substantially disk-shaped.

In another embodiment of the invention, the device includes an elastically deformable blade having a first portion that is held firmly in the internal chamber and a second portion that is movable between first and second positions in which the blade bears against respective ones of valve seats, depending on the deformation of the blade, with the moving portion thus defining the shutter.

The blade may be made of steel, for example.

The use of an elastically deformable blade can make it possible to avoid certain drawbacks associated with friction between the shutter and one or more portions of the drainage device when the shutter moves from one position to another.

The use of a blade also makes it possible to limit any risk of valve seats becoming obstructed.

Advantageously, the first and second valve seats are adjustable, in particular by being moved, so as to enable the first opening pressure and/or the closure pressure associated with a valve group to be adjusted.

The invention also provides a drainage device, in particular a device forming a hydrostatic switch, in particular for a drainage system as defined above, and comprising:
- an internal chamber;
- at least one inlet port and at least one outlet port, and optionally branch port communicating with the internal chamber;
- at least one shutter placed at least in part in the internal chamber;
- at least one first valve seat associated with the inlet port, the shutter being capable of bearing against the first valve seat in order to isolate the inlet port from the branch and outlet ports, in particular when the pressure difference between the inlet and outlet ports is less than a predetermined first opening pressure; and
- at least one second valve seat associated with the outlet port, the shutter being capable of bearing against the second seat in order to isolate the outlet port from the inlet and branch ports, in particular when the pressure difference between the inlet and outlet ports is greater than a predetermined closure pressure.

The invention also provides a drainage device suitable for use in particular in a drainage system as defined above, the device comprising:
- an internal chamber;
- at least one inlet port, at least one outlet port, and optionally a branch port, communicating with the internal chamber;
- at least one shutter placed at least in part in the internal chamber;

at least one first valve seat associated with the inlet port, the shutter being capable of bearing against the first seat in order to isolate the inlet port from the branch and outlet ports; and at least one second valve seat associated with the outlet port, the shutter being capable of bearing against the second seat in order to isolate the outlet port from the inlet and branch ports;

the device being characterized by the fact that the shutter comprises a ball, by the fact that the device includes a resilient return member arranged to exert a force on the shutter urging it to bear against the first seat, by the fact that the shutter is arranged to be capable of being moved towards the second seat against the force exerted by the resilient return member, and preferably by the fact that the resilient return member comprises a spring, in particular a spring including at least a conical or frustoconical portion.

The invention also provides a drainage device suitable for use in particular in the drainage system as defined above, the device comprising:

an internal chamber;

at least one inlet port and at least one outlet port, and optionally a branch port, communicating with the internal chamber;

at least one shutter disposed at least in part in the internal chamber;

at least one first valve seat associated with the inlet port, the shutter being capable of bearing against the first seat in order to isolate the inlet port from the branch and outlet ports; and at least one second valve seat associated with the outlet port, the shutter being capable of bearing against the second seat in order to isolate the outlet port from the inlet and branch ports;

the drainage system being characterized by the fact that it includes an elastically deformable blade having a first portion held firmly in the internal chamber and a second portion that is movable between first and second positions in which the blade bears against the first and second seats respectively, the movable second portion of the blade thus defining the shutter.

In the present description, if in the so-called "closed" position in which the shutter is shutting the flow constriction to the maximum extent, there exists a safety minimum flow rate between the shutter and the flow constriction, then the isolation or the closure are said to be "partial" (partial closure devices), otherwise it is considered that the isolation is total or that the closure is total.

The term "flow constriction" is used to designate the portion of the opening that can be shut by the shutter and that is associated with the outlet port, and optionally with a branch port, and that presents a minimum transverse area. The transverse area is measured perpendicularly to the general flow direction in the absence of the shutter. For an opening that is hourglass-shaped, the flow constriction thus designates the level where throttling is at a maximum.

It is considered that the shutter passes "through" the flow constriction when, by the shutter moving from upstream to downstream relative to said flow constriction, in particular under the effect of an increase in the pressure difference, the flow section between the flow constriction and the shutter passes through a minimum, and then possibly after being held at a constant minimum value, increases again. The minimum flow section of area S is obtained in the position in which the shutter provides maximum shutting of the flow constriction. Maximum shutting begins when the pressure difference reaches a closure pressure $P_f$ and is maintained until the pressure difference exceeds a "high-pressure" opening pressure $P_{HP}$. In the special circumstance of a shutter that is in the form of a ball, the ball passes "through" the flow constriction when its center passes through the plane, written $P_1$ in FIG. 13$b$, that is defined by the flow constriction.

Unless specified to the contrary, all of the flow rates mentioned in the present description are relative to deionized water at 37° C. Such water is a good model for the cerebrospinal liquid that is to be drained in operation.

The term "pressure difference" is used to designate the difference in pressure between the upstream and downstream sides of the device or system under consideration.

The present invention can be better understood on reading the following detailed description of non-limiting embodiments of the invention, and on examining the accompanying drawings, in which:

FIGS. 13$a$ to 13$c$ are diagrammatic section views showing a variant of a drainage device of the invention having a through shutter and shown in positions corresponding to increasing pressure differences;

In the various figures, identical references are used to designate members that are identical or analogous.

Figure 1:
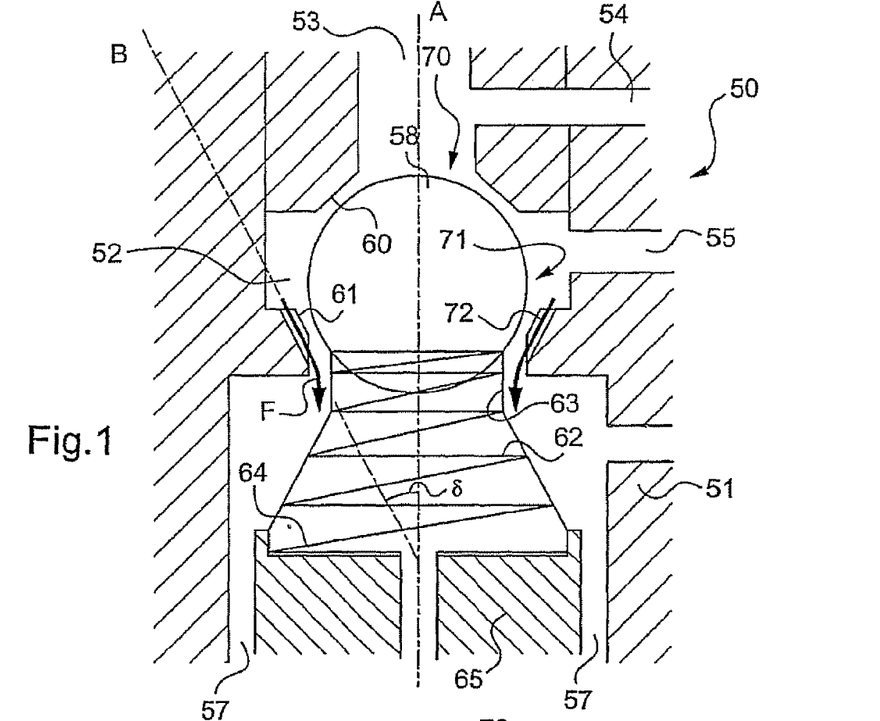
FIGS. 1 to 4 are diagrammatic and fragmentary section views showing various examples of drainage devices in accordance with the invention.

FIG. 1 shows a drainage device 50 comprising:

a body 51 defining an internal chamber 52;

an inlet port 53, branch ports 54 and 55, and lateral outlet ports 47, these ports communicating with the internal chamber 52;

a shutter 58 placed in the internal chamber 52, the shutter being formed by a ball, e.g. made of ruby or any other suitable material;

a first valve seat 60 associated with the inlet port 53, the ball 58 being capable of bearing against the first seat 60 in order to isolate the inlet port 53 from the branch port 55 and the outlet ports 57;

a second valve seat 61 associated with the outlet port 57, the ball 58 being capable of bearing against the second seat 61 in order to isolate, in full or in part, the outlet ports 57 from the inlet and branch ports 53, 54, and 55; and a resilient return member 62 formed by a spring arranged to act on the ball 58, applying a force urging it against the first seat 60, the shutter being movable towards the second seat 61 against the force exerted by the resilient return member 62.

The second seat 61 may be made on a portion of the body 51, or in a variant it may be formed on a washer that is assembled with the body 51.

At least one of the seats 60 and 61 can be made of metal, of ruby, of ceramic, or of plastics material, this list not being limiting.

By way of example, the spring 62, in particular a helical spring, may be made of metal and it may include, where appropriate, at least a portion that is cylindrical, conical, or frustoconical in shape.

By way of example, the spring 62 may include a cylindrical top portion 63 that is connected to a frustoconical bottom portion 64.

The spring 62 may also be of the spiral-wound flat type, for example.

The spring 62 is placed on a support 65 that can be adjusted in height in control the level of compression of the spring 62.

The ball 58 co-operates with the first valve seat 60 to define a first pressure-regulator valve 70 capable of opening at a first predetermined opening pressure $P_1$ to allow fluid to pass.

Where appropriate, the first valve seat 60 can be arranged to be slidably movable in order to set the first opening pressure $P_1$ to a desired value.

The ball 58 co-operates with the second valve seat 61 to define a second valve 71 that can close at a predetermined closure pressure $P_f$ greater than the first opening pressure $P_1$. This closure may be total, or as explained below, it may be only partial.

As can be seen, the first and second valves 70 and 71 enable cerebrospinal fluid to be drained effectively through the second valve 71 when the pressure of the fluid lies between the first opening pressure $P_1$ and the closure pressure $P_f$.

Since the height of the support 65 for the spring 62 is adjustable, it is possible to set the closure pressure $P_1$ to a desired value.

By way of example, the following may be true:

$$(P_f - P_1) < 2P_1, \text{ or } (P_f - P_1) < P_1, \text{ e.g. } P_f = 1.2\, P_1$$

The pressure difference that leads to the ball 58 being pressed against the second valve seat 61 is less than the pressure difference needed to lift the ball 58 off said seat. During closure of the valve, the cerebrospinal fluid flows around the ball 58, thereby accelerating its transfer to the second seat. This flow thus leads to suction downstream from the ball 58, thereby encouraging it to move towards the second valve seat 61. When the pressure difference reaches a determined closure pressure $P_f$, the ball 58 comes into contact with the valve seat 61. If the second valve closes completely, then the flow of cerebrospinal fluid becomes substantially zero in the maximally-shut, closed position in which the second seat is closed by the shutter. Subsequently, if the pressure difference decreases, the ball 58 will not lift off at the pressure $P_f$, but at a lower pressure, since there is no flow encouraging it to lift off. Such asymmetrical behavior between the valve closing and opening is referred to as "hysteresis".

The inventors have found that it is advantageous to maintain a minimum safety flow through the second valve when the valve is in its maximally-shut position. In particular, it is advantageous for this minimum safety flow to enable a "buffer" of cerebrospinal liquid to be maintained between the ball 58 and the valve seat 61. The directions A and B are preferably substantially parallel (FIG. 13*b*). The inventors have found that hysteresis is considerably diminished thereby.

In the embodiment shown in FIG. 1, where the ball 58 comes into contact with the seat 61, passages 72 can be provided to pass said minimum safety flow. The inventors have found that it is advantageous for the buffer of water that results from the cerebrospinal fluid flowing in the passages 72 to be locally oriented along the axis X.

Figure 13A:
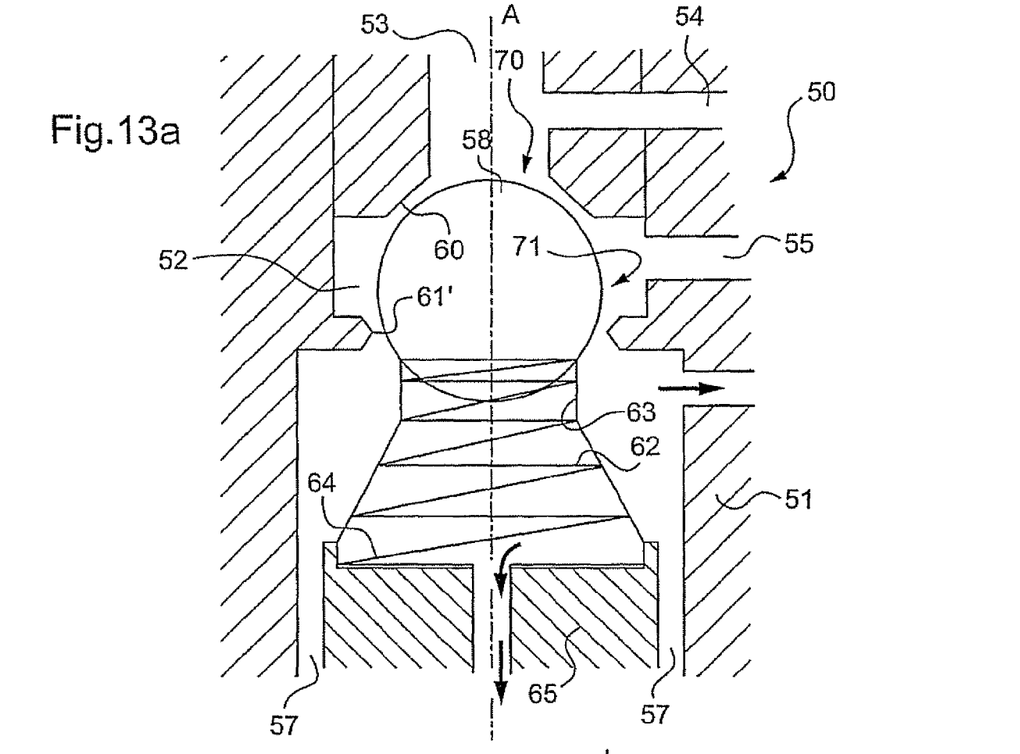
Figure 13B:
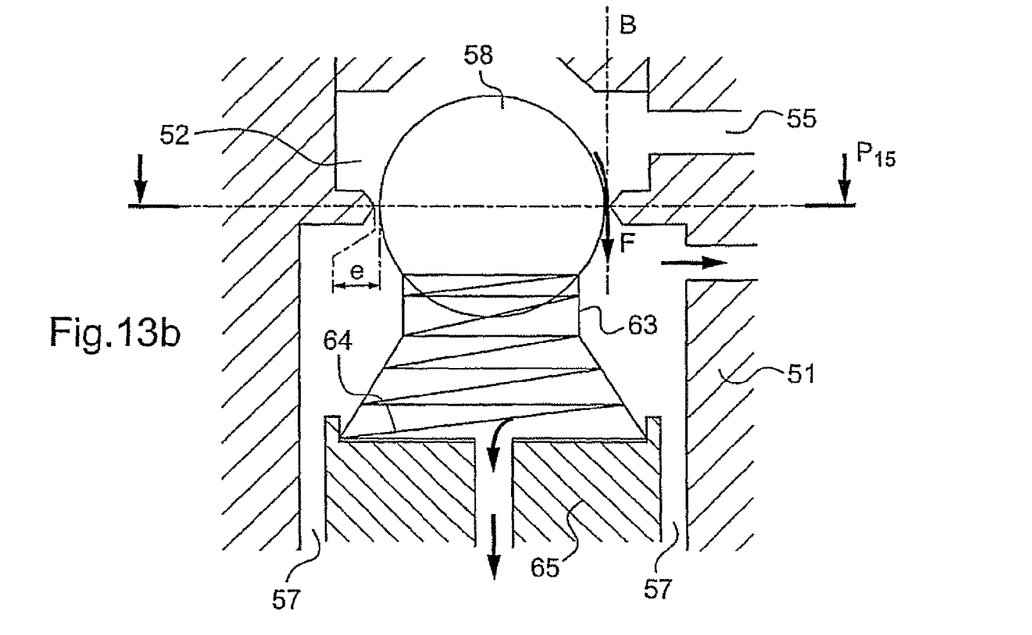
Figure 13C:
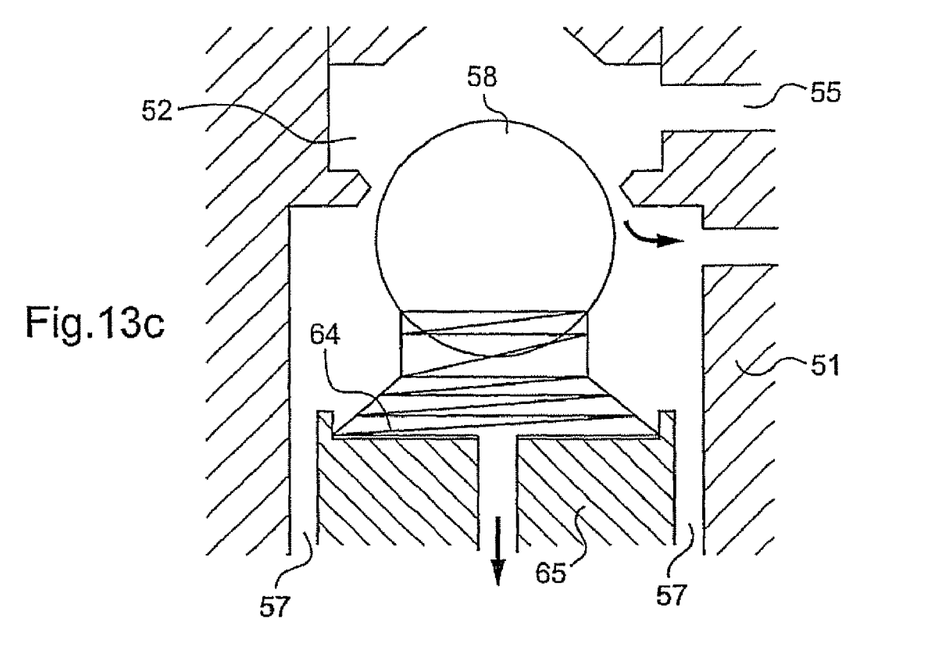
Figures 14, 15:
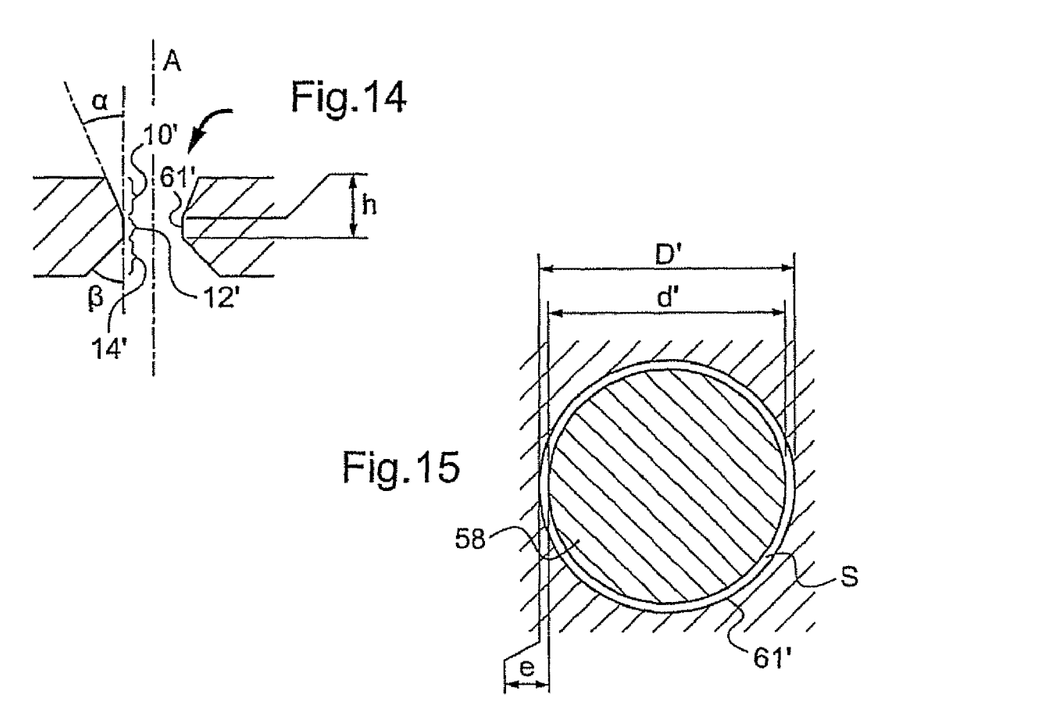
FIG. 14 is a diagrammatic longitudinal section through a second valve opening of an internal chamber of a drainage device in a preferred embodiment.
FIG. 15 is a cross-section on plane $P_{15}$ identified in FIG. 13$b$.

In another embodiment, shown in part in FIG. 13*a* and 13*c*, and also in FIG. 14, the constriction of the passage is not a valve seat, but an opening 61' shaped so as to allow the shutter to pass therethrough, specifically to allow the ball 58 to pass therethrough.

As shown in FIGS. 13*b* and 15, some minimum constant spacing e is provided in the maximally-closed position shown between the ball 58 and the flow constriction 61'.

The flow constriction 61' represents a circular shape of diameter D'.

Advantageously, this arrangement enables the risk of friction between the ball 58 and the flow constriction 61' to be limited. The hysteresis between opening and closing (maximum shutting) of the flow constriction is advantageously reduced thereby.

For the same reason, the ball 58 is carried by the spring 62 in such a manner as to move along a shift axis A that passes through the center of the ball 58 and that is substantially perpendicular to the flow constriction. Thus, regardless of the position of the ball 58, fluid flows symmetrically about the axis A, thereby ensuring the ball 58 is continuously self-centered on the axis A, particularly since the ball 58 is advantageously carried by a spring that allows it to move transversely a little. This configuration advantageously limits any risk of friction with the flow constriction 61'.

The embodiment shown in FIGS. 13*a* to 13*c* is advantageous. In the maximally-closed position shown in FIG. 13*b*, it makes it possible to establish a substantially cylindrical buffer of fluid about the axis A between the shutter and the flow constriction. Such a buffer is particularly advantageous for reducing hysteresis in the maximally-shut position.

In the zone of the flow constriction 61', the body presents the shape of an hourglass, as can be seen in the longitudinal section of FIG. 14. Going from upstream to downstream, this zone presents an upstream frustoconical section 10', a substantially cylindrical intermediate section 12' of height h, and a downstream frustoconical section 14'. The upstream frustoconical section 10' flares upstream with a half-angle at the apex equal to α. The downstream frustoconical section 14' flares downstream with a half-angle at the apex equal to β.

The upstream and downstream truncated cones meet in the substantially cylindrical intermediate section 12' that is coaxial about the axis A and that forms a surface of revolution about said axis.

The cylindrical section 12' which defines the flow constriction 61' can be of height h that is substantially zero ($P_f = P_{HP}$) as shown in FIGS. 13*a* to 13*c*. If it is of non-zero height (FIG. 14), the ball 58 can maintain a minimum flow through the second valve seat 61 while the pressure difference varies between the partial closure pressure $P_f$ and a high-pressure opening pressure $P_{HP}$.

The flow constriction 61' is preferably made of ruby. This confirmation further reduces the hysteresis effect.

Following a progressive increase in the pressure difference P between the inlet and outlet ports, the ball 58 occupies the following positions in succession:

When the pressure difference is small, the ball 58 presses in substantially leaktight manner against the first seat 60 so as to isolate the inlet port 53 from the outlet port 57. This closed position is conserved until the pressure difference reaches a predetermined first opening pressure $P_1$.

Above the first opening pressure, the ball 58 occupies successive positions (FIG. 13a) leading firstly to an increase in the flow rate D due to the ball 58 lifting off the first valve seat 60, and then preferably to a progressive decrease in said flow rate as a result of the flow constriction 61' shutting to an increasing extent. The flow rate decreases until the pressure difference reaches a closure pressure $P_f$ corresponding to a position in which the flow constriction 61' is maximally shut by the ball 58. In this position, the flow section through the flow constriction 61' is at a minimum (FIG. 13b).

Beyond the pressure $P_f$, the ball 58 begins to pass through the flow constriction 61'. If the flow constriction 61' presents a minimum flow section over a non-zero height h (FIG. 14), the flow is maintained at a minimum value so long as the pressure difference remains below a high-pressure opening pressure $P_{HP}$ that is greater than $P_f$.

When the differential pressure exceeds the closure pressure $P_f$, or where appropriate the high-pressure opening pressure $P_{HP}$, the ball 58 moves progressively away from the flow constriction 61', continuing its stroke downstream from the flow constriction (FIG. 13c). The flow rate through the drainage device then increases again.

The high-pressure opening pressure $P_{HP}$ can be defined in such a manner that the second valve opens in normal operation, i.e. apart from during cleaning stages.

The drainage device of the invention can thus advantageously, and alone, constitute a drainage system comprising:
an internal chamber;
at least one inlet port 53, at least one outlet port 57, and optionally a branch port, communicating with the internal chamber;
a ball 58 disposed in the internal chamber;
a first valve seat 60 associated with the inlet port 53, the ball 58 being capable of bearing against the first seat 60 so as to isolate the inlet port 53 from the outlet port 57;
a flow constriction 61' associated with the outlet port 57, the ball 58 being capable of blocking said flow constriction 61' in part in order to isolate the output port 57 in part from the inlet port 53; and
a resilient return spring 62 arranged to exert a force on the ball 58 along the axis A tending to press it against the first seat 60, and shaped in such a manner that the ball 58 lifts off the first valve seat 60 at a predetermined first opening pressure $P_1$, thus enabling fluid to pass through the seat;
the ball 58 being capable of being moved axially towards the flow constriction 61' against the force exerted by the spring 62 as far as a maximally-shut closed position corresponding to a pressure difference equal to a predetermined closure pressure $P_f$ that is greater than $P_1$, where the ball 58 co-operates with the flow constriction 61' to define a minimum flow section for passing fluid through the flow constriction 61';
the ball 58 also being capable of being moved axially beyond the flow constriction when the pressure difference exceeds a high-pressure opening pressure $P_{HP}$ that is greater than the closure pressure $P_f$.

The drainage device can thus provide a third valve for regulating pressure that opens at a second opening pressure equal to the high-pressure opening pressure $P_{HP}$ and greater than the closure pressure $P_f$. With such a device, and using a single shutter, it is thus advantageously possible to provide a three-valve drainage system as defined above.

The opening pressure $P_{HP}$ is then preferably determined in such a manner as to allow the drained flow rate to increase when the intracranial pressure or the hydrostatic pressure increases. The opening pressure $P_{HP}$ is preferably adjusted as a function of the needs of the patient.

In another embodiment, this function of increasing flow rate is provided by another pressure-regulator valve, e.g. of the Polaris® type that is connected in parallel with the drainage device. The high-pressure opening pressure can then be determined so that it is not reached under normal operating conditions, but only in the event of flush cleaning operations. For example, the high-pressure opening pressure may be set at 1 meter (m) of $H_2O$. Applying a pressure difference that is sufficient to enable the ball 58 to pass through the flow constriction 61' then advantageously enables effective cleaning operations to be performed, simultaneously in the flow constriction and in the valve that is connected in parallel with the drainage device, and with reduced risk of clogging by waste.

Figure 16:
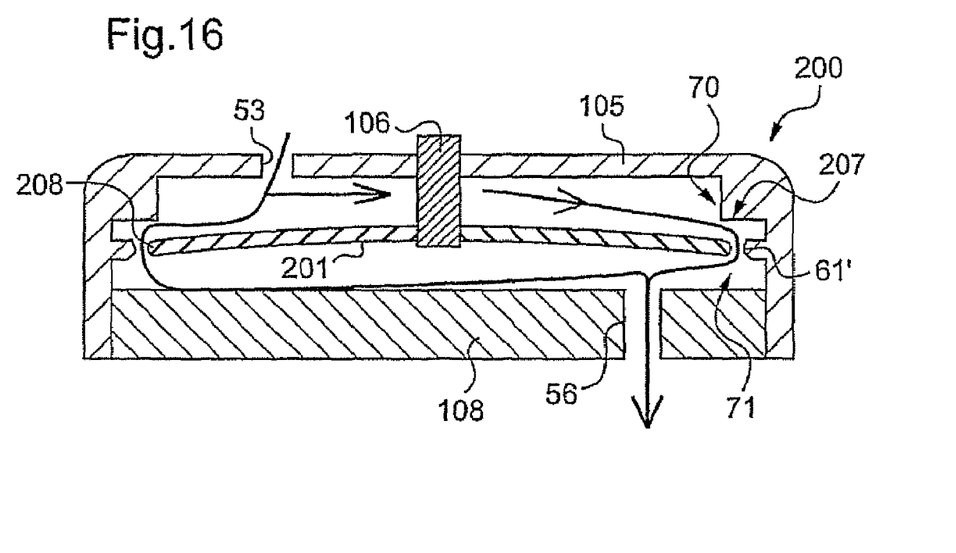
FIGS. 16 and 17 are diagrammatic longitudinal section views showing a variant diaphragm and a variant blade respectively for the drainage device of the invention with a through shutter.

In this embodiment, the valve connected in parallel with the drainage device is preferably adjustable. FIG. 16 shows another drainage device with a through shutter 200. This device comprises an elastically deformable diaphragm 201 that is held on a body 105 by means of a holder element 106 that is formed for example by a rod fastened to a central portion of the diaphragm 201. The holder element 106 can be arranged to be adjustable in position in translation in order to adjust the first opening pressure $P_1$ and the closure pressure $P_f$ associated with the valves 70 and 71. The body 105 has an annular shoulder 207 serving as a seat for the peripheral edge 208 of the diaphragm 201 for the first valve 70. It also has a flow constriction 61' that the peripheral edge 208 of the diaphragm 201 can move past when the pressure difference exceeds the closure pressure $P_f$.

When the pressure difference is less than an opening pressure $P_1$, the peripheral edge 208 of the diaphragm 201 bears in leaktight manner against the shoulder 207, thereby isolating the output port 56 from the inlet port 53. The first valve 70 is then closed. Once the pressure difference exceeds $P_1$, the valve 70 opens. The peripheral edge 208 of the diaphragm 201 then progressively closes the flow constriction 61' until this flow constriction 61' reaches a maximally-shut "closed" position, as shown in FIG. 16. Above the closure pressure $P_f$, the peripheral edge 208 moves away from the flow constriction 61' by going downstream therefrom.

Figure 17:
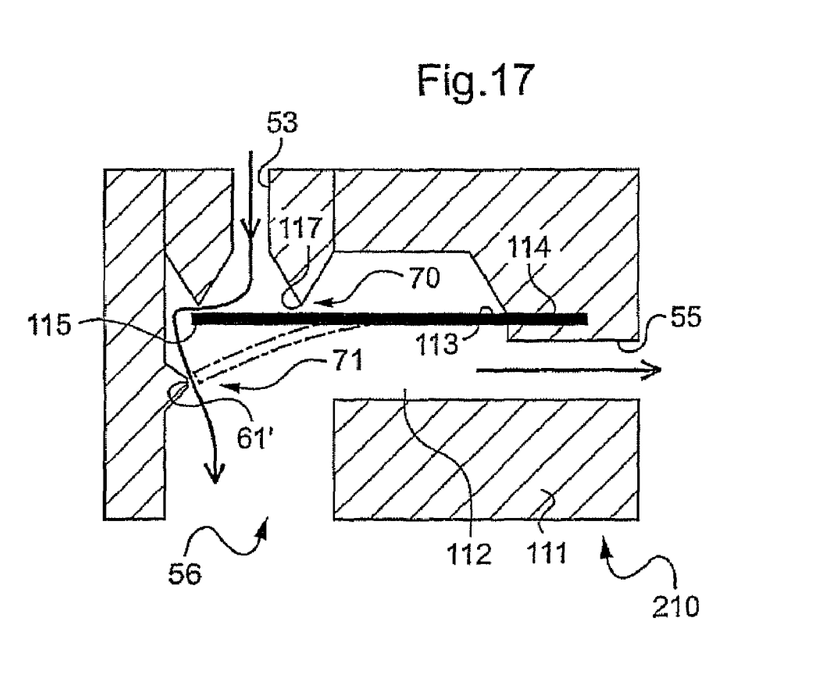

FIG. 17 shows yet another drainage device 210 with a through shutter. The drainage device 210 comprises:
a body 111 defining an internal chamber 112;
an inlet port 53, a branch port 55, and an outlet port 56, communicating with the internal chamber 112; and
an elastically deformable blade having a first portion 114 that is held firmly to the body 111, and a second portion 115 that is movable, constituting a shutter.

In a rest position, the portion 115 bears against a first seat 117, thereby isolating the inlet port from the branch port 55 and the outlet port 56.

When the pressure difference exceeds a first opening pressure $P_1$, the movable portion 115 separates from the seat 117, thereby putting the inlet port 53 into communication with the outlet port 56 and the branch port 55. When the pressure difference comes close to the closure pressure $P_f$, the peripheral edge of the blade comes close to a flow constriction 61' formed on the body 110. This constriction is shaped in such a manner that when the pressure difference reaches the closure pressure $P_f$ (dashed line), the flow section is at a minimum. Beyond the maximally-shut position of the flow constriction 61', as shown in FIG. 17, the peripheral edge of the blade 113 goes past the flow constriction 61', thereby allowing the flow rate to increase again.

Figure 2:
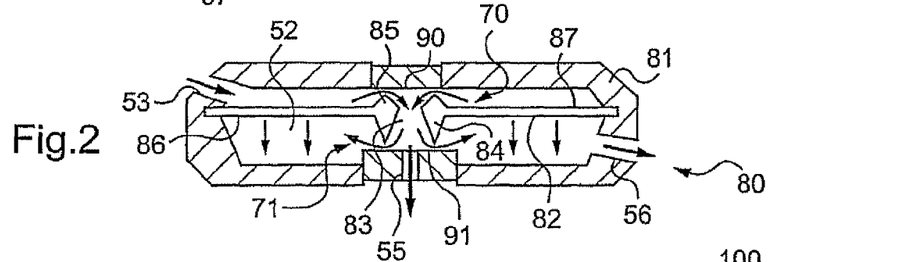

FIG. 2 shows another drainage device 80 comprising:
a body 81 defining an internal chamber 52;
an inlet port 53, a branch port 55, and an outlet port 56 communicating with the internal chamber 52;
an elastically deformable diaphragm 82, in particular made of elastomer, e.g. of silicone or of polyurethane, that presents substantially the shape of a disk and that includes a central passage 83 arranged to allow fluid to pass through, the diaphragm 82 also having annular bottom and top lips 84 and 85 around the central passage 83, the bottom and top lips projecting respectively from a bottom face 86 and a top face 87 of the diaphragm 82;
a first valve seat 90 against which the top lip 85 of the diaphragm 82 can bear when the diaphragm 82 is at rest, so as to isolate the inlet port 53 from the branch port 55 and the output port 56; and
a second valve seat 91 against which the bottom lip 84 can bear when the diaphragm 82 deforms sufficiently, so as to isolate the outlet port 56 from the inlet port 53 and the branch port 55.

By way of example, the lips 84 and 85 present a cross-section of triangular shape.

The diaphragm 82 is held against the body 81 via peripheral portion of the diaphragm 82.

The valve seats 90 and 91 are made for example out of a plastics material or out of metal, and they are arranged in such a manner as to be capable of being adjusted by sliding so as to make it possible firstly to adjust the level of the first opening pressure $P_1$ of the valve 70 formed by the top lip 85 and the valve seat 90, and secondly to adjust the level of the closure pressure $P_f$ for the second valve 71 formed by the bottom lip 84 and the seat 91.

Figure 3:
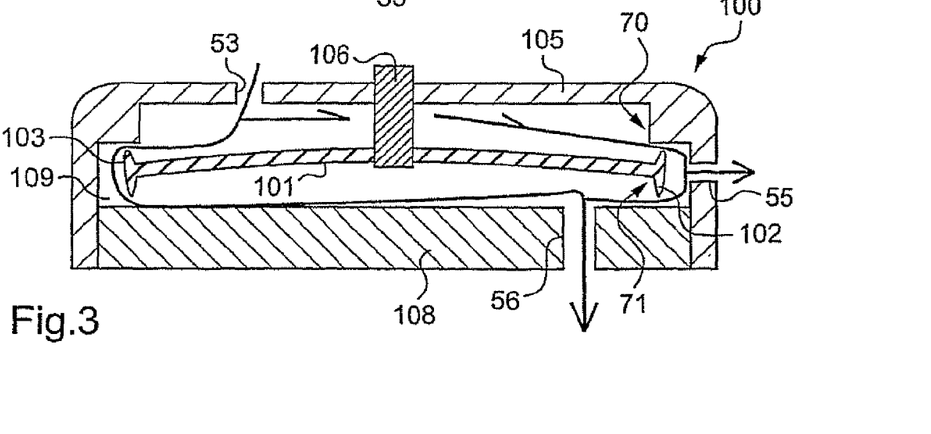

FIG. 3 shows another drainage device 100 that comprises, like the device 80, an elastically deformable diaphragm 101 provided at its periphery with bottom and top annular lips 102 and 103.

The diaphragm 101 is held against the body 105 of the device 100 via a holder element 106 that is formed, by way of example, by a rod fastened to a central portion of the diaphragm 101.

The holder element 106 may be arranged to be adjustable by movement in translation so as to adjust the first opening pressure $P_1$ and the closure pressure $P_f$ associated with the valves 70 and 71.

By way of example, the cross-sections of the lips 102 and 103 are triangular in shape and they are received in an annular setback 109 in the body 105.

The body 105 has a bottom portion 108 defining a valve seat for the lip 102, this portion 108 being movable in translation so as to adjust the closure pressure $P_f$ of the associated valve 71.

Figures 4, 5:
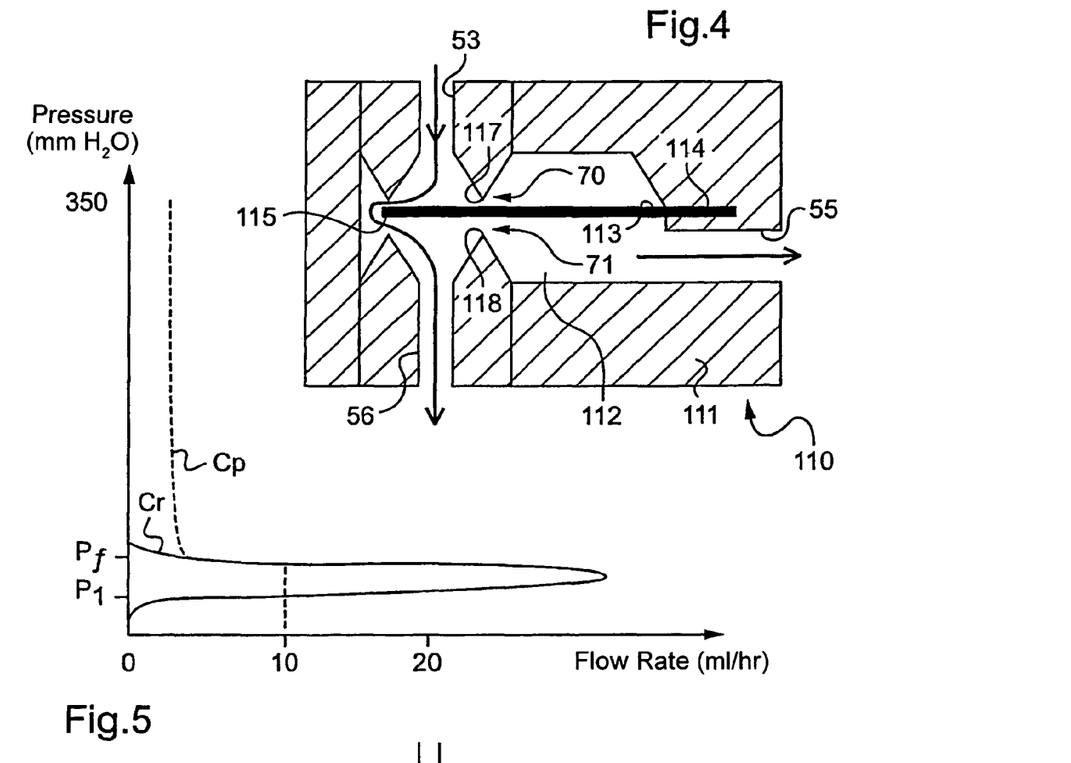
FIG. 5 is a graph showing the variation in flow rate as a function of the pressure applied between the inlet and the outlet of a device as shown in any one of FIGS. 1 to 4.

FIG. 4 shows a drainage device 110 comprising:
a body 111 defining an internal chamber 112.
an inlet port 53, a branch port 55, and an outlet port 56 communicating with the internal chamber 112; and
an elastically deformable blade 113 having a first portion 114 that is held securely to the body 111, and a second portion 115 that is movable between first and second positions in which the blade bears respectively against a first seat 117 and a second seat 118, the movable second portion 115 thus forming a shutter in the meaning of the invention.

By way of example, the seats 117 and 118 are formed by portions of cross-sections that are substantially triangular in shape.

By way of example, the seats 117 and 118 are made of elastomer, and can be arranged to be movable in translation so as to adjust firstly the first opening pressure $P_1$ of the valve 70 formed by the movable portion 115 of the blade 113 and the seat 117, and secondly to adjust the closure pressure $P_f$ of the second valve 71 formed by said movable portion 115 and the second seat 118.

When the movable portion 115 bears against the seat 117, the inlet port 53 is isolated from the branch port 55 and the outlet port 56.

When the movable portion 115 bears against the second seat 118, the outlet port 56 is isolated from the inlet port 53 and the branch port 55 which are in communication with each other.

The graph of FIG. 5 shows how pressure varies as a is function of the flow rate of fluid flowing through any one of the drainage devices 50, 80, 100, and 110, in embodiments with total shut off (curve $C_T$) or partial shut off (curve $C_P$) at the seat of the second valve.

The values marked on the graph are given by way of example, and other flow rate and pressure values could naturally be used.

In outline, the first valve 70 opens when the pressure of the cerebrospinal fluid reaches the first opening pressure $P_1$.

When the pressure of the fluid reaches the closure pressure $P_f$, the valve 71 closes either totally or partially.

Figure 6:
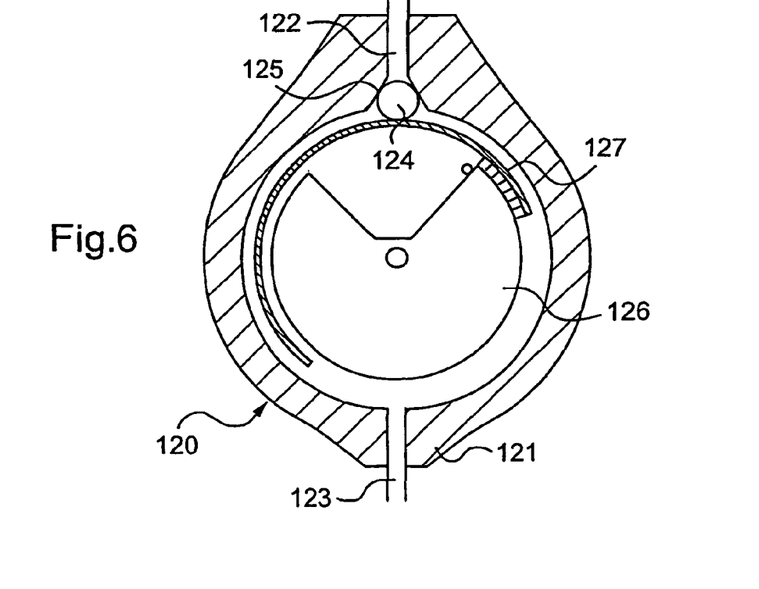
FIG. 6 is a diagrammatic and fragmentary section view of a pressure-regulator valve.

FIG. 6 shows an example of the third valve 120 for regulating pressure.

This valve 120 is described in detail in U.S. Pat. No. 4,673,384.

The valve 120 comprises a body 121, e.g. of plastics material, presenting an inlet port 122 and an outlet port 123.

The valve 120 has a shutter 124 formed by ball bearing against a seat 125 of the body 121.

The valve 120 also has a rotor 126 carrying a circularly-arcuate spring blade 127 that bears against the ball 124 so as to close the inlet port 122.

The inlet port 122 can be opened when the ball 124 is subjected to a second opening pressure $P_2$ that enables it to move away from the seat 125 against the force exerted by the spring blade 127.

The pressure-regulator third valve may be of any other type, e.g. it could have an elastically deformable diaphragm.

The third valve may be of a type that is adjustable from the outside so as to have a plurality of opening pressure levels, and it may optionally include a magnet.

Figures 7, 8, 9:
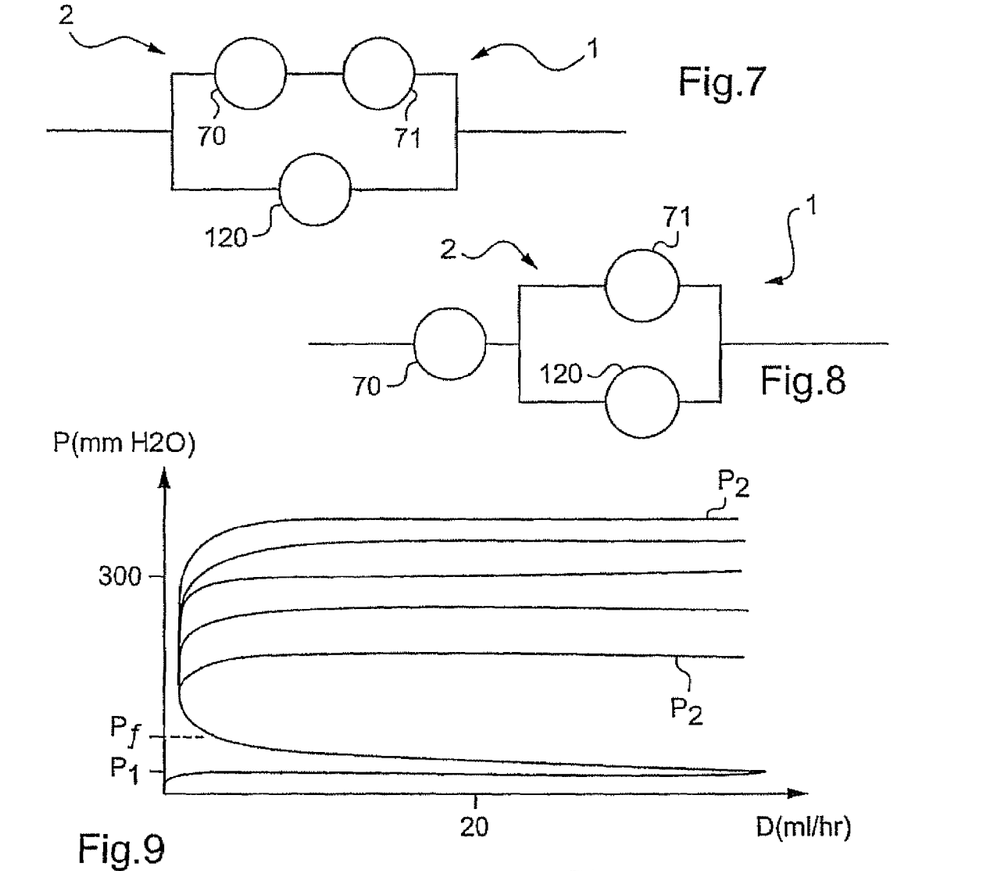
FIGS. 7 and 8 are diagrams showing various possible arrangements of valves suitable for forming a drainage system in accordance with the invention.
FIG. 9 is a graph showing the variation in flow rate as a function of the pressure applied to the systems of FIGS. 7 and 8.

FIG. 7 shows an example of the drainage system 1 for treating hydrocephalus, the system 1 comprising:
a group 2 of valves itself comprising:
a first valve 70 for regulating pressure that can open at a predetermined first opening pressure $P_1$ to allow fluid to pass; and
a second valve 71 that can close totally or partially at a predetermined closure pressure $P_f$ that is greater than the first opening pressure $P_1$, the first and second valves 70 and 71 being arranged in such a manner that the fluid can be drained through the second valve 71 when the pressure of the fluid lies between the first opening pressure $P_1$ and the closure pressure $P_f$; and
a third valve 120 for regulating pressure capable of opening at a second opening pressure $P_2$ that is greater than the closure pressure $P_f$, the second and third valves 71 and 120 being arranged in such a manner that when the second valve 71 is closed, fluid can be drained through the third valve 120 and optionally, if the second valve closes only partially, also through the second valve.

For example, the following may apply: $P_2 > 1.1 P_f$.

In the example shown in FIG. 7, the first and second pressures 70 and 71 are connected in series, the first valve 70 being upstream from the second valve 71, with the third valve 120 being connected in parallel with the assembly formed by the first and second valves 70 and 71.

In a variant, as shown in FIG. 8, the second and third valves 71 and 120 are connected in parallel, the first valve 70 being connected in series with the assembly formed by the second and third valves 71 and 120, upstream from said assembly.

The valves 70 and 71 are formed by any one of the devices 50, 80, 100, and 110.

The graph of FIG. 9 shows how flow rate varies as a function of pressure for the above-described system 1, the third valve 120 for regulating pressure being arranged to enable different levels to be obtained for the opening pressure $P_2$.

As explained above, a three-valve drainage system can also be made using a single shutter capable of passing through a flow constriction of the second valve, e.g. as shown in FIGS. 13a to 13c, 16, and 17.

When the valves 70 and 71 are closed by the drainage device 50 and the system 1 is in the configuration of FIG. 7, only the branch port 54 is used, which port is connected to the third valve 120.

In the configuration of FIG. 8, only the branch port 55 is used, which port is connected to the valve 120.

Figure 10:
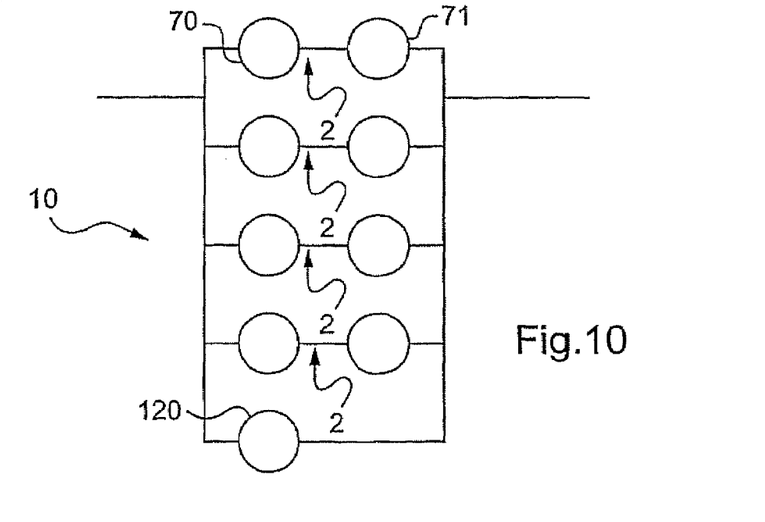
FIGS. 10 and 11 are diagrams showing two examples of arrangements of valves for making up drainage systems in accordance with the invention.

FIG. 10 shows a drainage system 10 constituting another embodiment of the invention, having a plurality of groups 2 of valves, each group comprising a first valve 70 for regulating pressure and a second valve 71.

In the embodiment shown in FIG. 10, the groups 2 and the third pressure 120 for regulating pressure are all connected in parallel.

Figure 11:
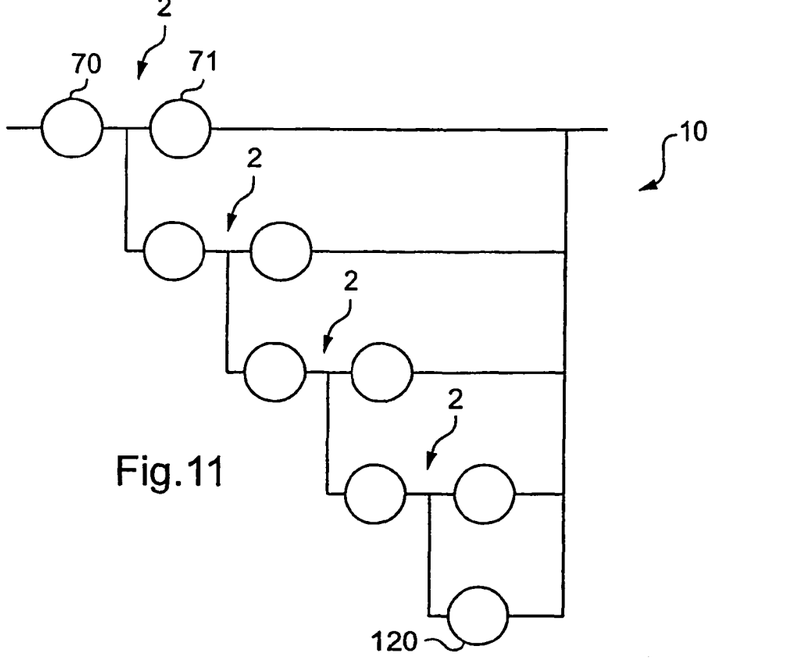

In a variant, as shown in FIG. 11, the valves 71 and 72 of a group 2 are connected in such a manner that the inlet port of the group 2 is connected to the branch port of another one of the valve groups 2.

The third valve 120 is connected to the branch port of one of the valve groups.

Figure 12:
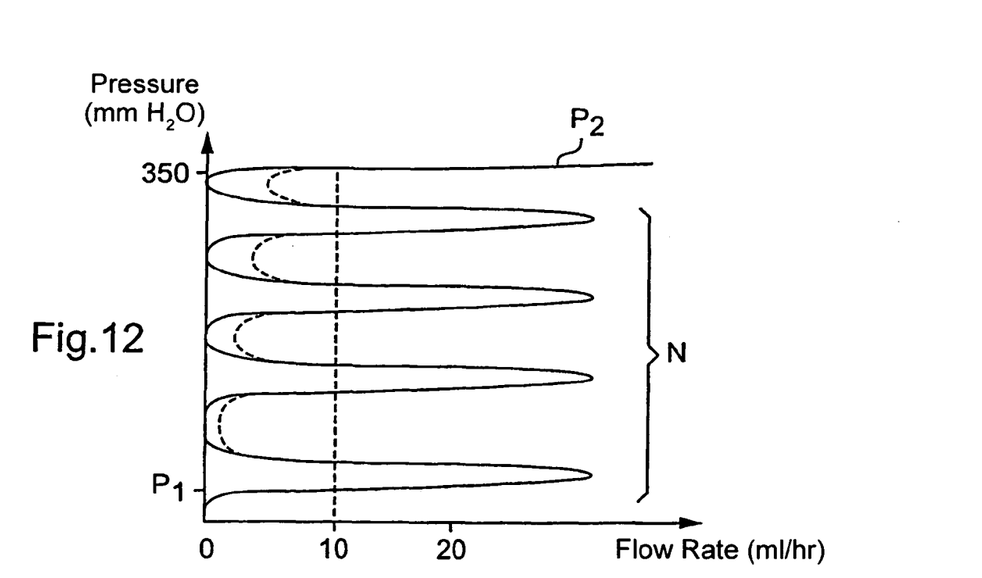
FIG. 12 is a graph showing diagrammatically how flow rate varies as a function of the pressure applied to the drainage systems shown in FIGS. 10 and 11.

The graph of FIG. 12 shows how pressure varies as a function of flow rate for the drainage system 10. The dashed line corresponds to said variation when the second valves 71 in the maximally-shut closed position allow a minimum safety flow rate of about 2.5 mL/h to pass.

The system 10 enables N opening and closure pressure levels to be obtained, by using the valve groups 2.

Thus, if so desired, the third valve 120 for regulating pressure may be of the single-pressure type.

The term "comprising a" should be understood as being synonymous with "comprising at least one" unless specified to the contrary.

Naturally, the invention is not limited to the embodiments described and shown. In particular, the preferred characteristics for the spring, for the diaphragm or the blade, or for the adjustment means described in the context of a drainage device presenting total closure could be applied to a drainage device presenting partial closure.

The invention claimed is:

1. A drainage device comprising:
    an internal chamber;
    at least one inlet port and at least one outlet port communicating with the internal chamber;
    at least one shutter disposed at least in part in the internal chamber;
    at least one first valve seat associated with the inlet port, the shutter being configured to bear against the first seat in order to isolate the inlet port from the outlet port when the pressure difference between the inlet and outlet ports is less than a predetermined first opening pressure; and
    at least one flow constriction associated with the outlet port, the shutter being configured to shut said constriction, while allowing a minimum, safety flow to pass at a rate that is greater than or equal to 2.5 mL/h even in a maximally-shut position, referred to as a "closed" position, which position is reached for pressure differences between the inlet and outlet ports that are greater than or equal to a predetermined closure pressure.

2. The drainage device according to claim 1, in which the shutter is in the form of a body of revolution.

3. The drainage device according to claim 2, in which the shutter comprises a ball, a return spring arranged to exert a force on the ball urging it against the first seat, the ball being arranged to be movable towards said flow constriction against the force exerted by the spring.

4. The drainage device according to claim 3, in which the spring includes at least a frustoconical base portion enlarging towards a bottom end of the spring, and a cylindrical top portion connected to said frustoconical base portion.

5. The drainage device according to claim 1, in which the shutter is movable relative to a body defining the internal chamber, the first seat and the flow constriction being stationary relative to said body.

6. The drainage device according to claim 1, in which the internal chamber presents a frustoconical shape upstream from the flow constriction, the frustoconical shape flaring upstream relative to a flow direction.

7. The drainage device according to claim 6, in which the internal chamber is extended downstream from the flow constriction by a truncated cone bearing downstream in the flow direction, with a half-angle at an apex β greater than a half-angle at an apex α of the upstream truncated cone.

8. The drainage device according to claim 1, in which the safety minimum flow rate is less than 20 mL/h.

9. The drainage device according to claim 1, shaped in such a manner that when the pressure difference increases, said shutter begins to reduce a flow rate through the first valve seat only if said flow rate lies in a range of from 15mL/h to 20 mL/h.

10. The drainage device according to claim 1, further comprising a branch port communicating with the internal chamber, the inlet and branch ports communicating with each other and being partially isolated from the outlet port by the shutter shutting the flow constriction.

11. The drainage device according to claim 1, in which the shutter and the flow constriction are shaped in such a manner that the shutter can pass through the flow constriction when the pressure difference exceeds a high-pressure opening pressure greater than said closure pressure.

12. The drainage device according to claim 11, in which said high-pressure, second opening pressure is at least 10% greater than said closure pressure.

13. The drainage device according to claim 11, in which the shutter can pass through the flow constriction without friction.

14. The drainage device according to claim 11, shaped in such a manner as to prevent a drainage flow rate greater than 20 mL/h if the pressure difference does not exceed said high-pressure opening pressure, and/or to guarantee a safety minimum flow rate of at least 5 mL/h when the pressure difference reaches or exceeds said closure pressure.

15. The drainage device according to claim 11, in which the shutter is in the form of a diaphragm or a blade.

16. The drainage device according to claim 1, in which the first opening pressure and/or the closure pressure and/or, where appropriate, a high-pressure opening pressure is or are adjustable, it being possible to perform said adjustment without contact.

17. The drainage device according to claim 16, further comprising either:
  a motor configured to enable the adjustment(s), the motor being configured to receive control instructions and/or power via radiofrequency waves, or
  means configured to enable magnetic coupling with an outside of a patient's body in order to perform the adjustment(s).

18. The drainage device according to claim 1, in which the flow constriction constitutes a second valve seat against which the shutter can bear, the shutter and the second valve seat forming a second valve that is configured to close at a predetermined closure pressure greater than the first opening pressure, while continuing to allow a safety minimum flow to pass at a rate greater than or equal to 2.5 mL/h.

19. The drainage device according to claim 18, further comprising at least one elastically deformable diaphragm having at least a portion that defines the shutter.

20. The device according to claim 19, the elastically deformable diaphragm including:
  a central passage arranged to allow fluid to pass through; and
  bottom and top lips substantially adjacent to the central passage, the bottom and top lips extending respectively from bottom and top faces of the diaphragm, the bottom and top lips configured to bear against respective ones of the valve seats as a function of a deformation of the diaphragm, the lips thus defining the shutter.

21. The device according to claim 20, in which the bottom and top lips extend close to or adjacent an outline of the diaphragm.

22. The drainage device according to claim 18, further comprising an elastically deformable blade having a first portion that is held firmly in the internal chamber and a second portion that is movable between first and second positions in which the blade bears respectively against the first seat and the second seat, the movable second portion of the blade thus defining the shutter.

23. The drainage device according to claim 1, in which the shutter and an edge of the flow constriction are shaped in such a manner as to define, in the maximally-shut position, a flow section between the shutter and the edge of the flow constriction such that the safety minimum flow rate in this position is greater than 5 mL/h, and less than 20 mL/h.

24. A drainage system for treating hydrocephalus, the system comprising:
  at least one group of valves comprising:
  a first valve for regulating pressure configured to open at a predetermined first opening pressure and allowing fluid to pass; and
  a second valve configured to close at a predetermined closure pressure greater than the first opening pressure while allowing a safety minimum flow at a rate greater than or equal to 2.5 mL/h, when closed, the first and second valves being arranged in such a manner that fluid can drain through the second valve when a pressure of the fluid lies between the first opening pressure and the closure pressure; and
  a third valve for regulating pressure configured to open at a predetermined second opening pressure that is greater than the closure pressure, the second and third valves being arranged in such a manner that fluid can be drained through the third valve when the second valve is closed.

25. The system according to claim 24, in which the first and second valves are connected in series, the first valve being upstream from the second, and the third valve is connected in parallel with the group formed by the first and second valves.

26. A system for treating hydrocephalus, the system comprising:
  at least one group of valves comprising:
  a first valve for regulating pressure configured to open at a predetermined first opening pressure and allowing fluid to pass; and
  a second valve configured to close at a predetermined closure pressure greater than the first opening pressure while allowing a safety minimum flow at a rate greater than or equal to 2.5 mL/h, the first and second valves being arranged in such a manner that fluid can drain through the second valve when a pressure of the fluid lies between the first opening pressure and the closure pressure; and
  a third valve for regulating pressure configured to open at a predetermined second opening pressure that is greater than the closure pressure, the second and third valves being arranged in such a manner that fluid can be drained through the third valve when the second valve is closed;
  in which the first and second valves are connected in series, the first valve being upstream from the second, and the third valve is connected in parallel with the group formed by the first and second valves, and
  the system including a drainage device according to claim 1, the shutter of said device co-operating with the first valve seat and with the flow constriction to define the first and second valves respectively of the group of valves.

27. The system according to claim 24, in which the second and third valves are connected in parallel and the first valve is connected in series with the assembly constituted by the second and third valves, upstream from said assembly.

28. A drainage system for treating hydrocephalus, the system comprising:
  at least one group of valves comprising:
  a first valve for regulating pressure configured to open at a predetermined first opening pressure and allowing fluid to pass; and
  a second valve configured to close at a predetermined closure pressure greater than the first opening pressure while allowing a safety minimum flow at a rate greater than or equal to 2.5 mL/h, the first and second valves being arranged in such a manner that fluid can drain through the second valve when a pressure of the fluid lies between the first opening pressure and the closure pressure;
  a third valve for regulating pressure configured to open at a predetermined second opening pressure that is greater than the closure pressure, the second and third valves being arranged in such a manner that fluid can be drained through the third valve when the second valve is closed; and
  a drainage device according to claim 11, the shutter of said device co-operating with the first valve seat to define the first valve and co-operating with the flow constriction to define the second and third valves.

29. The system according to claim 24, comprising a succession of valve groups, each being performed by a first valve for regulating pressure and by a second valve, the first opening pressure associated with the first valve of a given group being greater than the closure pressure associated with the second valve of the preceding group.

30. The system according to claim 29, comprising at least two valve groups, the two valve groups and the third valve all being connected in parallel.

31. The system according to claim 30, comprising at least two valve groups, each group having an inlet port, a branch port, and an outlet port, the inlet port of a first one of the groups being connected to the branch port of a second one of the valve groups, and the third valve being connected to the branch port of the first valve group.

* * * * *